United States Patent [19]
Sironi

[11] Patent Number: 6,093,474
[45] Date of Patent: Jul. 25, 2000

[54] PROCESS AND APPARATUS FOR MANUFACTURING INTERMEDIATE ABSORBENT PRODUCTS, AND ABSORBENT ARTICLES OBTAINED FROM SUCH PRODUCTS

[75] Inventor: Antonio Sironi, Carate Brianza, Italy

[73] Assignee: Korma S.p.A., Corso Italia, Italy

[21] Appl. No.: 08/406,919

[22] PCT Filed: Oct. 23, 1993

[86] PCT No.: PCT/EP93/02952

§ 371 Date: Mar. 27, 1995

§ 102(e) Date: Mar. 27, 1995

[87] PCT Pub. No.: WO95/03019

PCT Pub. Date: Feb. 2, 1995

[30] Foreign Application Priority Data

Jul. 21, 1993 [IT] Italy ................................. MI93A1612

[51] Int. Cl.[7] ..................................................... B32B 3/00
[52] U.S. Cl. ......................... 428/156; 428/188; 428/192; 428/206; 156/169; 156/176; 156/269; 156/271; 156/292; 156/510
[58] Field of Search .................................... 428/156, 188, 428/192, 206; 156/169, 176, 269, 271, 292, 510

[56] References Cited

U.S. PATENT DOCUMENTS

| | | |
|---|---|---|
| 3,399,671 | 9/1968 | Palatine . |
| 4,027,672 | 6/1977 | Karami ..................................... 128/284 |
| 4,699,808 | 10/1987 | Menard ................................... 427/180 |

FOREIGN PATENT DOCUMENTS

| | | |
|---|---|---|
| 2199479 | 4/1974 | France . |
| 1193433 | 6/1970 | United Kingdom . |
| WO9101217 | 2/1991 | WIPO . |

*Primary Examiner*—Christopher Raimund
*Attorney, Agent, or Firm*—Helfgott & Karas, P C.

[57] ABSTRACT

A process for manufacturing a continuous web-like intermediate absorbent product including the steps of depositing onto a web-like supporting sheet a predetermined pattern of absorbent material. Bonding the deposited absorbent material to the supporting sheet by means of heat. Depositing longitudinal strips of an adhesive material onto the web-like sheet. Applying at least a further web-like sheet over the assembly, which joins the further sheet to the former in correspondence of the adhesive strips by compression. Longitudinally slitting the web-like composite assembly obtained and separately winding into rolls the narrower webs obtained, which include adjacent absorbent cores.

13 Claims, 3 Drawing Sheets

PROCESS AND APPARATUS FOR MANUFACTURING INTERMEDIATE ABSORBENT PRODUCTS, AND ABSORBENT ARTICLES OBTAINED FROM SUCH PRODUCTS

TECHNICAL FIELD

The present invention relates to multilayer absorbent products and articles of the type incorporating two or more sheets of backing or containing materials between which absorbent materials in fibre, granule or powder form are sandwiched.

More particularly the present invention relates to a process and an apparatus for manufacturing an intermediate absorbent product, to be used in manufacturing finished or final absorbent articles, such intermediate product being formed by adjacent "absorbent cores" connected to each other by the sheets and being individually separable by slitting. The absorbent materials can be either conventional and well known materials, or the newer high-absorbency materials, such as the so called Super Absorbent Polymers (SAP).

The invention further relates to finished absorbent articles that are not to be re-used, i.e. to be disposed of after use, that incorporate products in accordance with the invention as a main absorbent core or pad, and that are obtained through conventional processes, e.g. by adding to such intermediate product cores one or more additional absorbent layers and/or containing sheets. Examples of such articles made up by two or more layers with a multiple structure are for example, feminine hygiene absorbents, infant diapers, incontinent briefs, absorbent sheets for foodstuff packaged in trays such as poultry, and more in general absorbent cloths for both household and industrial use.

For a better understanding of the invention, as used herein, the term "absorbent article" refers to a finished absorbent item that is ready to be used such as, for example, a flat sanitary towel, a diaper or a suitably dimensioned and shaped sheet adapted to be inserted in trays containing foodstuff.

On the other hand, as used herein, the term "absorbent product"—which is more directly related to the present invention—refers to a continuous absorbent web or ribbon of composite material, from which the finished absorbent articles are produced by adding further layers and/or sheets and by transversally and/or longitudinally cutting. The portion of the product used in an individual article is also referred to as absorbent core.

BACKGROUND ART

For manufacturing absorbent articles there are known the so-called "on line" processes, in which a continuous web is manufactured from which the article is cut out with as a segment of the desired length. These processes are typically employed for disposable articles such as baby diapers and feminine hygiene products. This kind of products incorporates cellulose fibres and superabsorbent polymers (SAP) either in fibre or powder form, that are blended up or arranged to form one of more layers, with the absorbent materials being sandwiched between sheets of tissue paper or the like, peripherally folded and bonded, or glued on such sheets and forming one or more layers. More particularly, in feminine hygiene products, SAP powders are bonded onto cellulose-based substrates (i.e. air-laid paper) and afterwards enveloped or wrapped by the substrates.

This process has the disadvantage of a limited width of the absorbent product, generally narrower than 600 mm, and of a poor flexibility since only a limited number of article configurations can be obtained. The number of layers in the absorbent article is limited, typically only one layer is provided when using SAP powders, and moreover such powders have to be encapsulated, which causes further technical restrictions.

Moreover, this known process is quite difficult to be modified to cope with future production requirements since even small modifications of the article involve substantial process changes with the associated high levels of investment and cost. Further, in many cases line modifications are unfeasible due either to existing space restraints or to the complexity of the employed process, or in case to a relative complexity of the desired product.

According to another known process, the absorbent article is manufactured through a separate (off line) process which delivers large sheets of laminated or composite material from which the desired absorbent articles are formed by slitting.

These composite or laminated sheets are formed from a large variety of components and/or materials. Typically, sheets of different materials such as, for example, tissue-paper and air-laid paper, nonwovens fabrics of different types, synthetic films and the like are joined together by thermal, chemical and/or mechanical bonding means. In case SAP materials are used, either as powders or fibres, they are evenly or randomly distributed over the supporting fabrics or included between them.

Although the so obtained products can have a considerable width (over 1,000 mm), nevertheless this kind of processsn has other disadvantages.

More particularly, when such laminated products are further treated or slit down to form articles that are smaller or have particular configurations, their edges cannot be protected any longer, nor joined together for effectively retaining the powders or the fibres that can migrate in large amount out of the absorbing portion until reaching the external surface of the finished article, which renders the products totally unacceptable for sanitary purpose and in the food industry.

Furthermore, all of these processes have a reduced absorbing capacity, particularly when SAP materials in fibre, granule or powder form are used. As it is well known, these materials exhibit their highest absorbency in a loose condition, i.e. when they are neither made adhered to supporting sheets, nor compressed by a calendering. On the other hand the absorbent materials must remain in their designated areas of use, which requires a certain degree of fixing or bonding between the materials and the substrates. The two requirements are conflicting with each other, so that the products (and the articles) presently obtained by the known processes are in general unsatisfactory, the more so when SAP materials are being used.

SUMMARY OF THE INVENTION

An object of the present invention is to provide a process that overcomes the above-mentioned limitations and shortcomings of the prior art, and more particularly that allows to achieve, by means of an off-line process, intermediate multilayer absorbent products, incorporating powders or fibres or granules of absorbent materials, which products may also be of small size, with the maximum design flexibility and without appreciable additional costs for modifying the shape or the structure of the absorbent article.

Another object of the invention is to provide an apparatus for manufacturing an absorbent product of the aforementioned type that is simple and flexible, with the absorbent articles that are easily obtained from such intermediate product.

A further object of the invention is to provide a final absorbent article of the above-mentioned type, obtained from an intermediate absorbent product wider than 1,000 mm by slitting portions with the desired size, and with a thickness depending on the number of the layers and the configurations selected for the incorporated absorbent material.

The process and apparatus of the present invention offer to the manufacturer of absorbent articles an extended variety of choice in developing and producing absorbent articles, substantially without any additional cost for modifying the production plant.

According to the invention, the layers of absorbent material are kept in the desired locations and in accordance with the selected pattern, by longitudinally glueing together the sheets containing them, and by a partial glueing thereof (to the supporting sheets) thanks to a bonding agents blended with the absorbent material.

The article according to the invention which is obtained from the intermediate product has a high flexibility of design in respect of the distribution of the absorbent materials between the containing sheets, as well as a high flexibility in respect of the structure which can comprise up to five containing sheets. Finally, in the intermediate product which is preferably stored in rolled form, each portion intended to form the absorbent core of an article will be separated from the adjacent one by a bonding line.

BRIEF DESCRIPTION OF THE DRAWINGS

The invention will now be described with reference to preferred but not limited embodiments, illustrated in the attached drawings, in which.

DETAILED DESCRIPTION OF PREFERRED EMBODIMENTS

Figure 1:
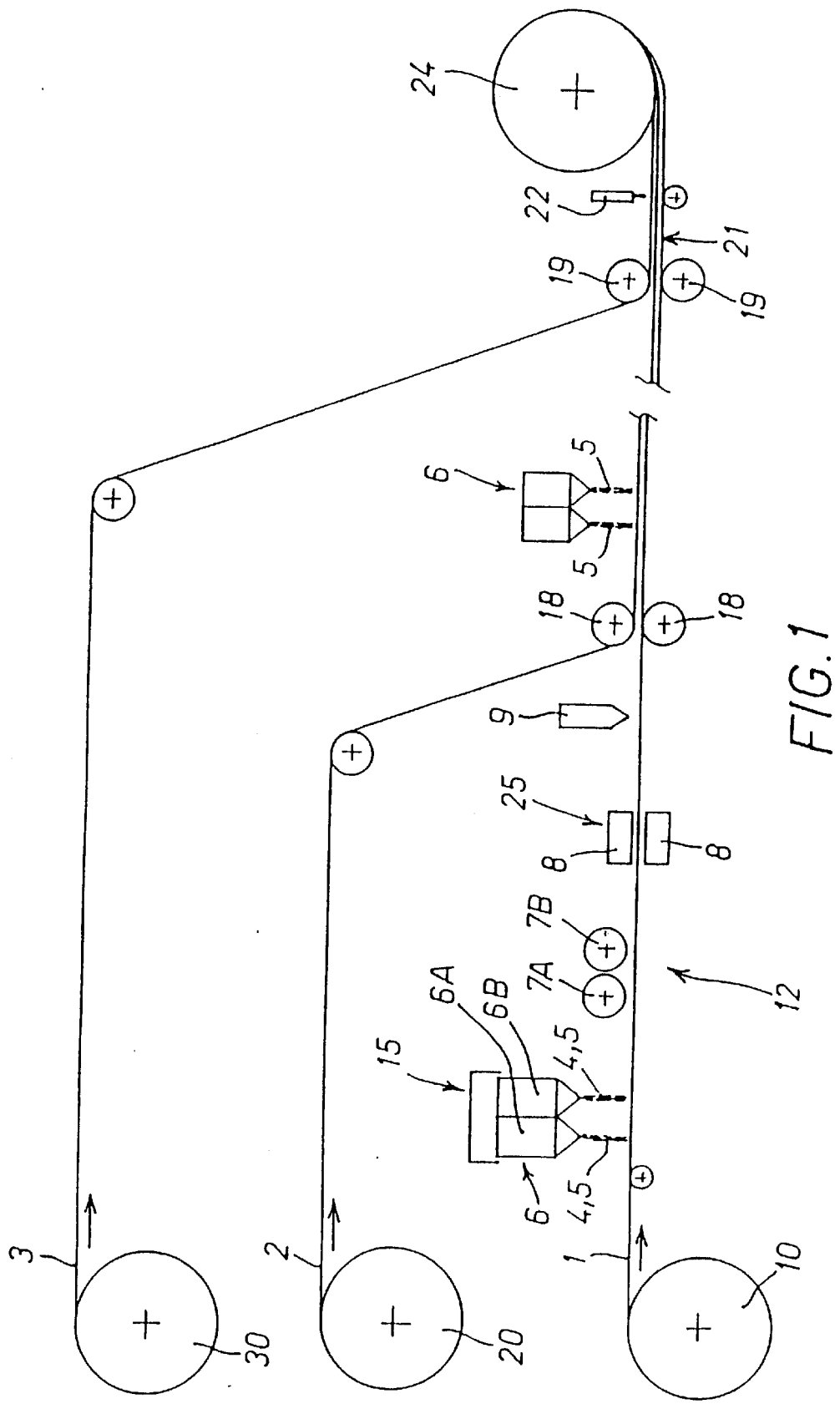
FIG. 1 schematically shows an embodiment of an apparatus for manufacturing intermediate absorbent products comprising three sheets for containing absorbent material.

With reference to FIG. 1, the manufacturing apparatus according to the invention comprises a production line 12 fed by three reels 10, 20 and 30 of a web-like containing and supporting material 1, 2 and 3, respectively. Each webs is indicatively larger than 1000 mm and its width is a function of the specific applications.

Onto the web material 1 fed from reels 10, an amount of absorbent material 5 is deposited in accordance with predetemined configurations or patterns at a depositing station 15. The deposition is achieved by means of a dispenser 6 comprising two containers 6A and 6B arranged in sequence from which the materials are being poured.

The material of each supporting sheet 1, 2 and 3 can be any well-known conventional material used in the manufacture of absorbent articles, such as a substrate of woven fabric, of nonwoven fabric or felt, of cellulose-based materials, e.g. a cellulose air-laid or wet-laid material, in case provided with perforations, or tissue paper, or a synthetic film either perforated or not. The density of each fabric is preferably in a range from 10 $g/m^2$ to 300 $g/m^2$.

The dispenser 6 is provided with two hopper-shaped containers 6A and 6B, disposed side by side along the machine direction and capable of laying predetermined amounts of absorbent material 5, either in powder, fiber or granulate form, onto the underlying sheet 1.

The absorbent material 5 can be either a single absorbent material or a blend of absorbent materials, that is capable of turning into a gel upon being wetted, and thus to retain large amounts of liquids with respect to its own original volume.

Preferred materials in this respect are the so-called Super Absorbent Polymers or SAP, in particles, powders or elongated fibres form, however, according to the invention other known absorbent materials can be used, both in powders and fibres form. Typically, the size of the particles in a powder material are in a range of 40 to 1,400 microns, whereas above such upper limit, they are more properly referred to as granules or fibres.

The density of the deposited absorbent material, measured in the product and with respect to the deposited areas, is preferably from $10/g/m^2$ to 1,000 $g/m^2$.

Figure 2:
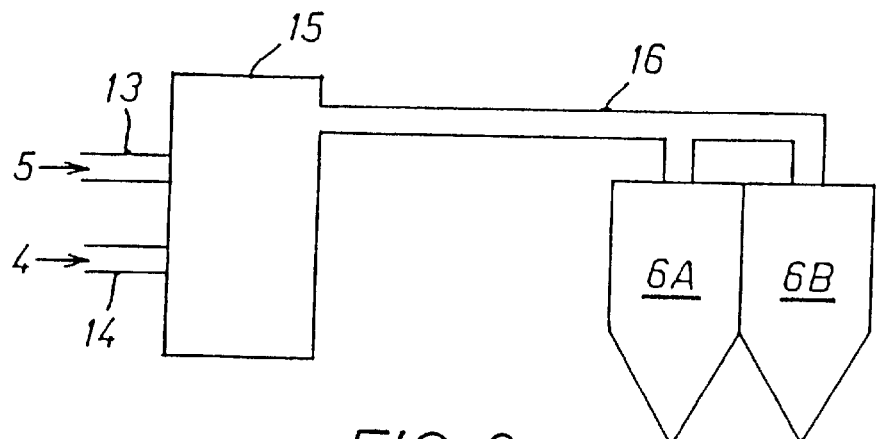
FIG. 2 shows an embodiment of the absorbent material dispenser.

According to a preferred embodiment of this invention, and with particular reference to FIG. 2 showing the dispenser, the absorbent material 5 is blended in advance with a bonding agent 4, in particle, fiber or powder form, which can be activated by application of heat. Such bonding agent 4 is either a thermoplastic polymer such as polypropylene, polyethylene, ethylene vinyl acetate or other synthetic or natural bonding agent. The amount of the bonding age is from 3% to 30% by weigth of the absorbent material 5. The blending takes place in a mixer 15 fed with suitable flow rates of the substances through tubes 13 and 14, and the mixer in turn feeds the two dispensers 6A and 6B through a tube 16.

According to an alternative embodiment of the present invention (not shown), the absorbent material and the bonding agent are deposited as two separate layers, by separately feeding the two dispensers, i.e. one with the absorbent material and the other with the bonding agent. In case the absorbent material is fed to the container 6A, that is located upstream of dispenser 6B, the bonding agent layer is formed above the absorbent material, whereas in the opposite case the bonding agent layer is directly deposited over the support 1.

Immediately downstream of the deposition station 15, rollers 7A, 7B are provided for locally removing the SAP or other absorbent material in order to form desired patterns or configurations of the absorbent material adapted to improve the absorbing effect. Then the web 1 passes through a sticking station 25 provided with means 8 for applying heat such as, for example, an infrared oven, or heaters capable of blowing hot air, or other known devices.

According to a further embodiment, the means 8 are adapted to direct hot steam onto the web 1 to activate the surface of the deposited absorbent material 5, thus rendering the material tacky, and in this case no bonding agent is deposited on web 1.

At a subsequent glueing station a dispenser 9 applies longitudinal lines or stripes 11 of an adhesive material onto the web 1. The material forming such adhesive strip 11 can be a so called hot-melt comprising various material, such as APP, SBS, SEBS, SIS, EVA, etc., or a cold glue, such as a dispersion of various material, e.g. SBS, natural rubber, etc, or even a solvent-based or a two-components adhesive system. The amount of adhesive is a function of the type of adhesive used, however it is generally comprised between 0.2 and 20 g/meter.

Downstream of the dispenser 9, two calibrating or pressure rollers 18 join together the web-like sheet 2 from reel 20 and the sheet 1, thus covering and enclosing between them the absorbent materials 5 without any appreciable compression thereof. The joining of the two sheets occurs along the adhesive strips 11.

Downstream of the rollers 18, the apparatus provides for an arrangement that is substantially similar to the one already illustrated, with a deposition station, rollers for locally removing the SAP material, a sticking station and a glueing station that are substantially similar to the previous ones and therefore will not be further described.

At the end of this second portion of the apparatus in which it is further provided the joining together of the assembly 1-5-11-2 with the web-like sheet 3 by means of calibrating rollers 19, in the embodiment shown by FIG. 1 an intermediate absorbent product 21 is obtained. Downstream of rollers 19, cutters 22 (e.g. a comb-shaped blade) are disposed for longitudinally slitting and dividing the product into narrower composites, that are subsequently winded in rolls, one of which being designated by numeral 24. The longitudinal slits occurr along the internal strips 11.

The apparatus according to the invention can of course comprise more than three feeding reels, with the corresponding plant portions 6-7-8-9, in order to manufacture products (and therefore articles) with more than three supporting and containing sheets.

Figure 3:
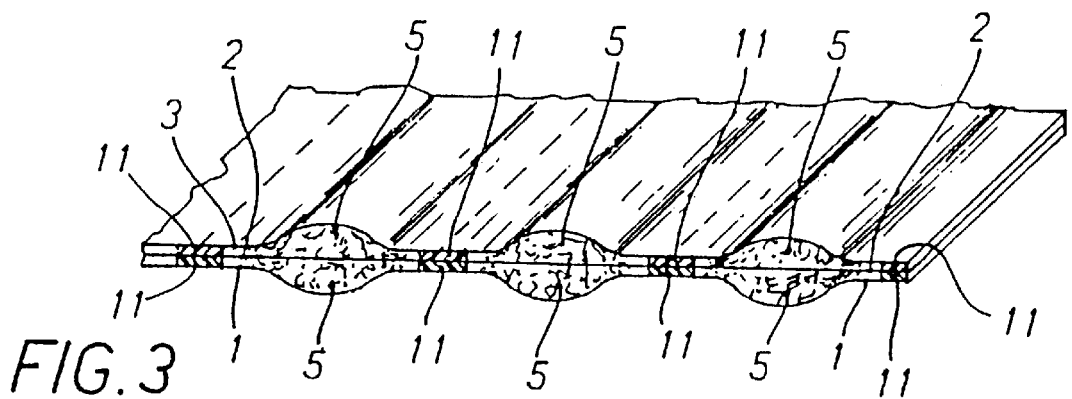
FIG. 3 is a perspective view, partially cross-sectioned, showing a portion of a product obtained in accordance with the process of the invention.
Figure 4:
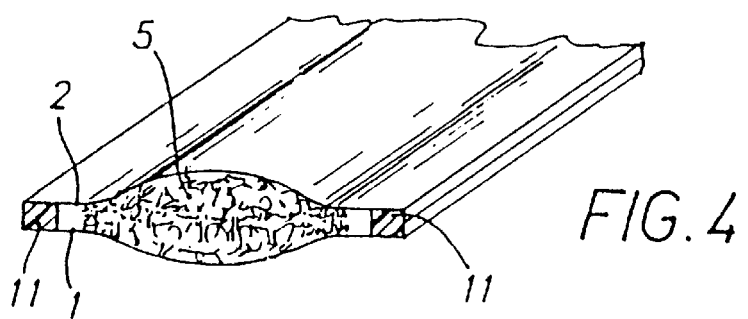
FIG. 4 is a perspective view of a single absorbent core of the intermediate product according to the invention.

FIGS. 3 to 5 show cross-section views of the structure of some absorbent products manufactured according to the invention, with the same numerals of FIG. 1 being used for designating equal or similar components.

FIG. 3 shows a cross-section perspective view of a product manufactured through the apparatus of FIG. 1, comprising patterns of the absorbent material 5 sandwiched between containing sheets 1, 2 and 3 and adhesive strips 11 longitudinally located therebetween. In the Figure the absorbent product has not yet been slit to form the individual absorbent articles.

The absorbent material patterns (and in case of the bonding agent blended therewith) are schematically shown as rectangular, however within such general outline it is possible to obtain inner areas of desired shape without the absorbent material which has been removed, e.g. by suction.

FIG. 4 shows a perspective view of the structure of a individual absorbent which has been longitudinally slit from the product, and includes a pattern 5 of absorbent material incorporating the bonding agent, sandwiched or encapsulated between two sheets 1, 2 and laterally closed by adhesive strips 11.

Figure 5A:
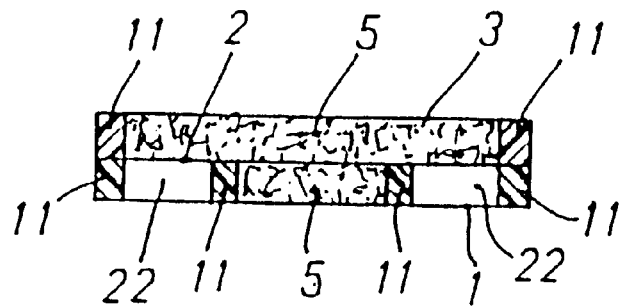
FIGS. 5A to 5C are cross-section views showing possible embodiments of the absorbent articles manufactured according to the invention.
Figure 5B:
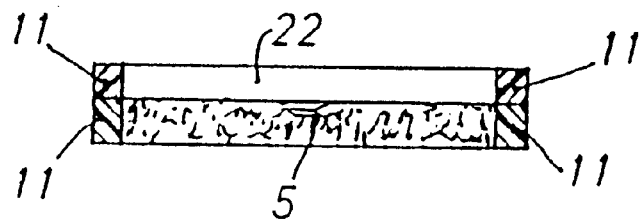
Figure 5C:
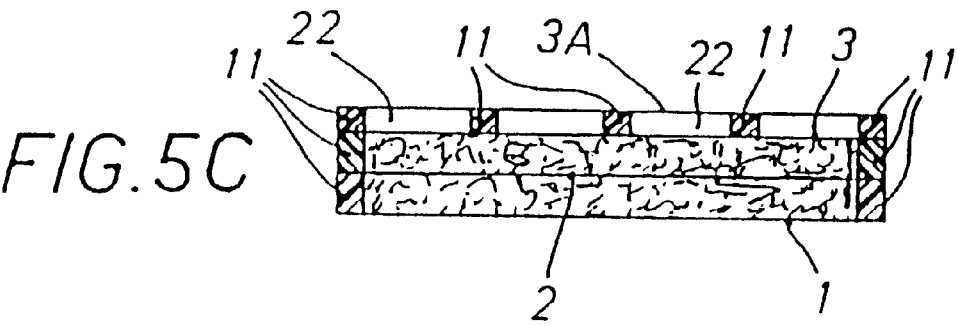

FIGS. 5A to 5C show some possible embodiments of absorbent articles according to the invention, in which are used the same numerals of the previous Figures.

It is to be noted that thanks to the invention it is possible to obtain either uniform layers or random layers of absorbent material, as well as areas without absorbent material that form gaps designated with 22. These gaps or hollow spaces can extend either for the whole width of the product or the article (FIG. 5B), or only for a part thereof (FIG. 5A), so as to form preferred passages for the liquids to be absorbed by the material 5.

What is claimed is:

1. A process for manufacturing a continuous web-like intermediate absorbent product comprising an absorbent material in powder, granule or fiber form, placed between containing sheets, the process comprising the steps of:
   a. depositing onto a flat exposed surface of at least one continuous web-like supporting sheet fed from a feeding reel, a layer of absorbent material in accordance with a predetermined pattern;
   b. bonding, by means of heat, said deposited absorbent material to the web-like supporting sheet;
   c. depositing longitudinal strips of an adhesive material onto said web-like supporting sheet;
   d. applying at least a further web-like sheet over the assembly joining said further web-like sheet to said supporting sheet in correspondence with said adhesive strips by compression;
   e. longitudinally slitting an obtained web-like composite assembly, and
   f. separately winding into rolls the narrower webs so obtained which comprise adjacent absorbent cores.

2. A process as claimed in claim 1, wherein said layer of absorbent material is deposited after being blended with a bonding agent in powder, granule or fiber form, said agent being activated to be in condition by applying heat thereto.

3. A process as claimed in claim 2, wherein said bonding agent comprises a thermoplastic polymer.

4. A process as claimed in claim 3, wherein said thermoplastic polymer is selected from the group consisting of polypropylene, polyethylene and ethylene vinyl acetate.

5. A process as claimed in claim 1, wherein a bonding agent that can be activated by applying heat is deposited in form of powder, granules or fiber and with the same pattern of the absorbent material, directly over the supporting sheet, or over an already deposited absorbent material.

6. A process as claimed in claim 1, wherein in order to bond the absorbent material to the supporting sheet, the surface of the absorbent material is activated by means of steam that renders the material tacky.

7. A process as claimed in claim 1, wherein said absorbent material includes at least one superabsorbent polymer (SAP).

8. A process as claimed in claim 1, wherein the material of said at least one supporting sheet is selected from the group consisting of woven fabric, nonwoven fabric, synthetic film, tissue paper, and air-laid paper.

9. An apparatus for manufacturing a web-like intermediate absorbent product including absorbent materials in powder, granule or fiber form, sandwiched between supporting sheets, comprising:
   at least two feeding reels of a web-like supporting material;
   at least one dispenser for depositing a predetermined pattern of absorbent material in powder, granule or fiber form onto a web-like material sheet unrolled and fed from one of said reels;
   means for supplying heat for bonding said absorbent material to said sheet onto which it has been deposited;
   dispensing means for depositing longitudinal strips of an adhesive material onto said sheet;
   pressure means for applying a further web-like sheet and joining it to said web-like material sheet;
   one or more cutters for longitudinally dividing the so obtained web product into narrower composite webs;
   gathering means for winding into rolls said narrower composite webs comprising adjacent absorbent cores.

10. An apparatus as claimed in claim 9, wherein said dispenser delivers a blend formed of an absorbent material and a bonding agent.

11. An apparatus as claimed in claim 9, further comprising means for selectively and locally removing said absorbent material in order to obtain desired patterns of said absorbent material.

12. A continuous web-like intermediate absorbent product comprising a predetermined pattern of absorbent material sandwiched between supporting sheets manufactured through a process according to claim 1.

13. A multilayer absorbent article including absorbent material in powder, granule or fiber form, manufactured from the intermediate product according to claim 12 and using a portion of said intermediate product as an absorbent core.

* * * * *